Figure 1:
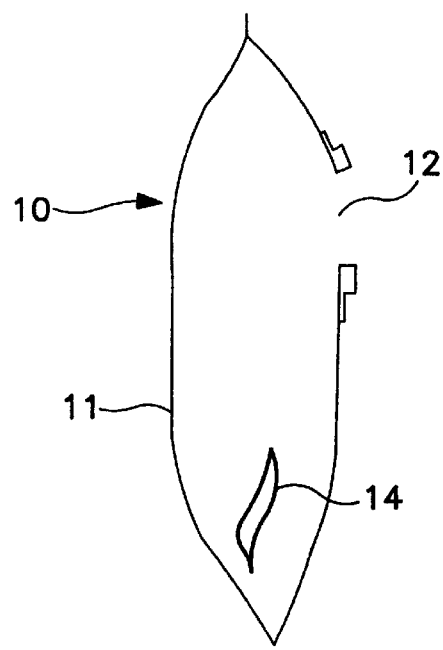

United States Patent [19]
Gent

[11] Patent Number: 5,860,959
[45] Date of Patent: Jan. 19, 1999

[54] CONTROLLED RELEASE OF ADDITIVES IN AN OSTOMY POUCH OR BAG

[75] Inventor: John A. Gent, Liphook Hants, England

[73] Assignee: Bristol-Meyers Squibb Company, Princeton, N.J.

[21] Appl. No.: 800,245

[22] Filed: Feb. 13, 1997

[51] Int. Cl.[6] .................................................. A61F 5/44
[52] U.S. Cl. ........................ 604/332; 604/333; 604/327
[58] Field of Search .................................. 604/327, 332, 604/333

[56] References Cited

U.S. PATENT DOCUMENTS 2,800,905  7/1957  Simmons et al. ..................... 604/333
5,411,496  5/1995  Homa ..................................... 604/333

Primary Examiner—Robert A. Clarke
Attorney, Agent, or Firm—Stuart E. Krieger

[57] ABSTRACT

The malodours of an ostomy bag are reduced by including therein an article including a hygroscopic matrix and additive. The matrix is selected from polyethylene glycol, polypropylene glycol and glycerol. The additive is selected from food preservatives, fragrances, disinfectants, and odor absorbers.

9 Claims, 1 Drawing Sheet

CONTROLLED RELEASE OF ADDITIVES IN AN OSTOMY POUCH OR BAG

This invention relates to ostomy bags and to a method of reducing maladours.

When body waste is excreted into an ostomy bag the waste will continue to break down with the release of malodours. Therefore, when an ostomate removes the bag he or she encounters malodours which are often unpleasantly strong and embarrassing. Certain substances, herein called additives, can be used to reduce this odour. These include:

malodour counteractant fragrances;

water absorbing materials such as starch and superabsorbents (e.g. alkali metal polyacrylates);

anti-microbial agents such as disinfectants;

food preservatives;

odour absorbers such as volcanic clays; and chemical reactants.

Two methods by which these are added to an ostomy bag are known to be in commercial usage, namely:

in liquid form and aqueous form and in tablet capsule form.

In the former case a liquid such as a fragrance may be added to the bag immediately prior to the patient wearing the bag. If disinfectants or preservatives are used, these are often added in aqueous solutions which significantly reduce the capacity of the bag to contain the body waste.

In the case of tablet capsule addition it is essential for the tablet to breakdown and to release its active components before it becomes submerged under body waste. The lack of success of such products in ostomy bags, hitherto, is due to a combination of failure of the tablet to adequately breakdown and/or contact the majority of the body waste. In consequence, tablet addition to the ostomy bag usually fails to achieve the desired effect of minimising or masking malodours.

The additives referred to above become functional (i.e. reduce malodours) when they are contacted by aqueous media from body waste. In the case of urine this contains adequate free aqueous matter to activate and distribute these additives throughout the bag contents. In the case of ileal fluid, there is significantly less free water, but in most cases sufficient to enable said additives to be distributed throughout the bag contents. In the case of colostomy waste there is only available a small amount of free water which is normally inadequate for said additives to be activated and thus distributed throughout the bag contents. It would be desirable if there existed a method by which these additives can be activated and distributed throughout the bag. It has been surprisingly found that one can utilise the fact that the atmosphere in a colostomy bag has a high humidity by virtue of the presence of a stoma and body waste contents.

According to one aspect of the present invention, there is provided a method of reducing malodours produced in an ostomy bag which comprises inserting into the bag an article, for example a strip, having a surface area of not significantly less than about 10 cm², said article comprising a hygroscopic composition comprising a hygroscopic matrix and additives which on exposure to a temperature of not less than 37° C. and at least 90% relative humidity absorbs water at a rate of greater than 10 grams per square metre per hour, to form a liquid layer which distributes additives within the bag;

said hygroscopic matrix being selected from one or more of the following materials:

polyethylene glycol;

polypropylene glycol;

glycerol and per 100 parts by weight of said matrix there being present 1 to 80 parts by weight of said additives, said additives being selected from one or more of the following classes of materials:

food preservatives;

malodour counteractant fragrances;

disinfectants; and odour absorbers.

According to another aspect of the present invention, there is provided an ostomy bag designed to reduce malodours therein, which contains an article, for example a strip, having a surface area of not significantly less than about 10 cm², said strip comprising a hygroscopic composition comprising a hygroscopic matrix and additives which on exposure to a temperature of not less than 37° C. and at least 90% relative humidity absorbs water at a rate of greater than 10 grams per square meter per hour, to form a liquid layer which distributes additives within the bag; said hygroscopic matrix being selected from one or more of the following materials:

polyethylene glycol;

polypropylene glycol;

glycerol;

and, per 100 parts by weight of said matrix, there being present in said bag 1 or 80 parts by weight of said additives which are selected from one or more of the following classes of materials:

food preservatives;

malodour counteractant fragrances;

disinfectants;

odour absorbers;

the bag further containing a material capable of absorbing water such as starch or a superabsorbent.

Within an ostomy bag, when it is being worn in use, there is a temperature of about 37° C. and a high humidity. The high humidity will arise from both the stoma itself, and any body waste in the bag. This high humidity can be utilised if a hygroscopic composition is placed within the bag. The hygroscopic composition can take up water from the atmosphere in the bag and from contacting the body waste. It has been found that it is possible to use compositions which in the dry state have melting points in excess of 43° C., (110° F.) but which readily absorb water at the high humidity in the bag, causing it to form a cream or solution at a temperature of about 37° C. The hygroscopic composition physically changes, and will progress from a solid through a viscous to a water like consistency as water is progressively absorbed. Into this hygroscopic composition are blended one or more of the additives mentioned previously.

According to a further aspect of the invention, there is provided a method of reducing malodours in an ostomy bag which comprises associating a malodour counteractant fragrance with a hygroscopic carrier, the carrier being one which, when subjected to high humidity and a temperature above about 37° C., releases the malodour counteractant fragrance within the bag.

According to a yet further aspect of the invention, there is provided an ostomy bag which contains a water-soluble, skin-compatible, strip carrying or embodying a hygroscopic composition which has a melting point below 37° C. but greater than ambient temperature, the said composition containing a malodour counteractant fragrance.

In a preferred aspect of this invention it is desirable that the hygroscopic composition should have as large a surface area as is possible.

Figure 2:
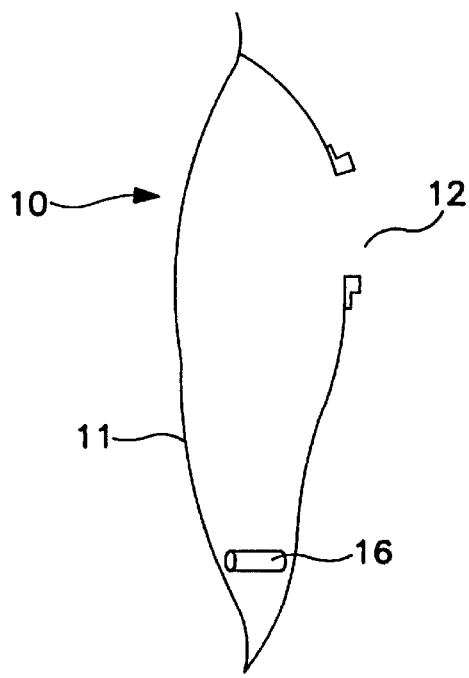

FIG. 1 is a schematic drawing of a cross-sectional view of an ostomy bag containing a strip of malodour counteractant, pursuant to the present invention; and FIG. 2 is a schematic drawing of a cross-sectional view of an ostomy bag containing a molded article of a malodour counteractant, pursuant to the present invention.

In use, the hygroscopic composition provides a controlled release of the additive(s). In one form, it is preferred that the hygroscopic composition is in the form of or is carried by a flat strip. The strip may have a total surface area of at least 10 sq. cm., and preferably each side has a surface area of hygroscopic composition of at least 5.5 sq. cm. The absorption of water occurs at a rate proportional to the surface area of the strip. A fibre reinforcement of the hygroscopic composition may be included to prevent the hygroscopic composition breaking up by mechanical damage. The fibre reinforcement may comprise a lightweight cellulose paper tissue. As another alternative system polyethylene glycol in solid form, containing additives as referred to above, may be included in the ostomy bag.

In an alternative form, the hygroscopic composition may be in the form of, or be carried by, a moulded article. For example, the article may be in the form of a dodecahedron, or a similar lozenge shape.

By way of illustration, FIGS. 1 and 2 show schematically a malodour counteractant article placed in a conventional ostomy pouch 10. The pouch 10 consists of an envelope 11 having a stomal aperture 12. In FIG. 1, a strip 14 made in accordance with the present invention is shown in the ostomy bag 10. In FIG. 2 a molded article in the shape of a tablet 16, in accordance with the present invention, is shown in the ostomy bag 10.

EXAMPLE 60 g of polyethylene glycol of molecular weight 2000 is heated at 60° C. to form a clear molten liquid. To this molten liquid is added, by stirring, 40 g of an encapsulated malodour counteractant comprising of approximately equal parts by weight of starch and fragrance (i.e. additive). Said product is then metered onto a supporting cellulose fibre tissue of weight 17 gsm to yield a product having a weight per unit area of about 900 gsm. The product is allowed to cool and solidify. A strip measuring approximately 80 mm×20 mm×2 mm this is cut from the product and exposed to 90% relative humidity and a temperature of 37° C. (98° F.), which would be representative of that encountered in a colostomy situation. After 30 minutes it was found that the surface of the strip had absorbed 0.09 grams of water and had a cream-like consistency which was easily removed from its surface.

It has been observed that initially the absorption of the water vapour takes place preferentially on the surface of the strip of tablet. This yields a fluid layer whilst the 'core' of the strip remains solid. This fluid layer may be removed from the surface of the strip very easily by wiping. This aspect is important. When the bag is in use, as a consequence of body movement of the wearer, one film surface of the bag will move relative to the other, thereby causing the fluid layer to smear across the film surface. It is believed that the presence of this fluid surface when faecal discharge occurs, enables said faecal matter to easily slide across the strip and take with it a portion of the fluid layer thereby improving the distribution of additives in the bag. As a result, malodours are reduced.

The delivery system, whereby the additives gain quick and effective access to the faecal material in the bag, is preferably a tablet/pill or a strip, which may be placed in the ostomy bag prior to bag usage. An alternative technique can be adopted whereby a coating is applied to the inner surface of the bag, at the fabrication stage. This coating may be continuous, or in the form of stripes or in the form of dots or patches. The aim of this technique is to improve and, ideally, maximise, the opportunity for the additives to contact the faecal surface.

An effective method of delivering additives into an ostomy bag, involves delivering them from a matrix, which is characterised by being solid at room temperature, and which delivers additives by removing water from the atmosphere within the ostomy bag and/or the body waste. As a result, there is formed an aqueous solution or dispersion of additives, which interacts with the body waste to reduce the level of malodours evolved in an ostomy bag.

A preferred matrix comprises 100 parts by weight of one or more hygroscopic components, such as polyethylene glycol, polypropylene glycol and glycerol together with 1 to 80 parts by weight of additives as referred to above. Alternatively, a matrix which includes "dots" of adhesive to which odour-absorbing granules are bonded may be employed. As regards this suggestion, the reader is referred to U.K. Patent Application No. 2,268,685A.

Examples of additives to counter malodours include fragrances, oxidizing agents, for example, water soluble persulfates, peroxides, nitrates, chlorates and permanganates of ammonia and alkali metals, odour absorbing granules, e.g. volcanic clay, alumina, silica gel, odour absorbing polymer particles and carbonaceous particles such as activated carbon granules, benzaldehyde, copper sulphate, sodium bicarbonate, calcium carbonate, trisodium phosphate or sodium carbonate. Other possibilities for use as counteractants to malodours are various preservatives and anti-oxidants. In this connection, the reader is referred to the list of preservatives and anti-oxidants set out on pages 175/6 of the book "Understanding Additives" published jointly by Consumers Association and Hodder & Stoughton. These listed preservatives and anti-oxidants are deemed to be incorporated herein by reference.

According to an advantageous feature of the invention, substances having disinfecting and bactericidal properties are incorporated in the hydroscopic matrix together with the malodour counteractant. This prevents or reduces the possibility that bacteria may grow within the bag and cause fermentation and hence odour. Suitable bactericides will be known to a man of average skill in the art.

It will be understood that the invention may be carried out in other ways, and that the claims herein are not intended to be limited to the particular details set out in the specific description.

I claim:

1. A method of reducing malodours produced in an ostomy bag which comprises inserting into the bag an article having a surface area of not significantly less than 10 cm$^2$, said article comprising a hygroscopic composition comprising a hygroscopic matrix and additives which on exposure to a temperature of not less than 37° C. and at least 90% relative humidity absorbs water at a rate of greater than 10 grains per square metre per hour, to form a liquid layer which distributes additives within the bag; said hygroscopic matrix being selected from one or more of the following materials:

polyethylene glycol,
polypropylene glycol;
glycerol
and per 100 parts by weight of said matrix there being present 1 to 80 parts by weight of said additives, said additives being selected from one or more of the following classes of materials:

food preservatives;

malodour counteractant fragrances, disinfectants; and odour absorbers.

2. An ostomy bag, designed to reduce malodours therein, which contains an article having a surface area of not significantly less than 10 cm², said article comprising a hygroscopic composition comprising a hygroscopic matrix and additives which on exposure to a temperature of not less than 37° C. and at least 90% relative humidity absorbs water at a rate of greater than 10 grams per square metre per hour, to form a liquid layer which distributes additives within the bag; said hygroscopic matrix being selected from one or more of the following materials:

polyethylene glycol, polypropylene glycol;

glycerol;

and, per 100 parts by weight of said matrix, there being present in said bag 1–80 parts by weight of said additives which are selected from one or more of the following classes of materials:

food preservatives;

malodour counteractant fragrances;

disinfectants;

odour absorbers;

the bag further containing a material capable, of absorbing water such as starch or a superabsorbent.

3. The ostomy bag according to claim 2, wherein the article comprises a strip.

4. The ostomy bag according to claim 3 wherein the strip is a thin flat strip having length and breadth each less than 40 mm and a thickness of from 1.5 to 3 mm.

5. The ostomy bag according to claim 3 in wherein the strip embodies a cellulose fibre tissue which supports the hygroscopic matrix.

6. The ostomy bag according to claim 2, wherein the article is in the form of a lozenge.

7. The ostomy bag according to claim 2 wherein the hygroscopic matrix principally comprises polyethylene glycol.

8. The ostomy bag according to claim 2 wherein the hygroscopic matrix principally comprises polypropylene glycol.

9. The ostomy bag according to claim 2 in which the hygroscopic matrix principally comprises glycerol.

* * * * *